United States Patent
Uziel et al.

(10) Patent No.: US 9,297,692 B2
(45) Date of Patent: Mar. 29, 2016

(54) SYSTEM AND METHOD FOR INSPECTING A SAMPLE USING LANDING LENS

(71) Applicant: APPLIED MATERIALS ISRAEL, LTD., Rehovot (IL)

(72) Inventors: Yoram Uziel, Misgav (IL); Alon Litman, Nes-Ziona (IL); Ofer Adan, Rehovot (IL); Ron Naftali, Shoham (IL); Juergen Frosien, Riemerling (DE)

(73) Assignee: Applied Materials Israel, Ltd., Rehovot (IL)

( * ) Notice: Subject to any disclaimer, the term of this patent is extended or adjusted under 35 U.S.C. 154(b) by 353 days.

(21) Appl. No.: 13/772,287

(22) Filed: Feb. 20, 2013

(65) Prior Publication Data

US 2014/0231632 A1    Aug. 21, 2014

(51) Int. Cl.
| | |
|---|---|
| G01J 1/02 | (2006.01) |
| G01J 1/04 | (2006.01) |
| G01N 21/88 | (2006.01) |
| G02B 21/00 | (2006.01) |
| G02B 21/24 | (2006.01) |
| G01N 21/95 | (2006.01) |
| G01N 21/956 | (2006.01) |
| G02B 13/00 | (2006.01) |

(52) U.S. Cl.
CPC .............. G01J 1/0266 (2013.01); G01J 1/0422 (2013.01); G01N 21/8806 (2013.01); G02B 21/0016 (2013.01); G02B 21/24 (2013.01); G01N 21/9501 (2013.01); G01N 21/956 (2013.01); G02B 13/001 (2013.01)

(58) Field of Classification Search
USPC ........ 850/9, 24; 250/201.3; 977/869; 348/79, 348/80; 359/368–398, 656–661
See application file for complete search history.

(56) References Cited

U.S. PATENT DOCUMENTS

| | | | |
|---|---|---|---|
| 2004/0070846 A1* | 4/2004 | Dobschal et al. ............. | 359/795 |
| 2006/0262419 A1* | 11/2006 | Harada ......................... | 359/656 |
| 2008/0130103 A1* | 6/2008 | Hara et al. .................... | 359/369 |

* cited by examiner

*Primary Examiner* — Renee D Chavez
(74) *Attorney, Agent, or Firm* — Kilpatrick Townsend & Stockton LLP

(57) ABSTRACT

An evaluation system that includes a miniature module that comprises a miniature objective lens and a miniature supporting module; wherein the miniature supporting module is arranged, when placed on a sample, to position the miniature objective lens at working distance from the sample; wherein the miniature objective lens is arranged to gather radiation from an area of the sample when positioned at the working distance from the sample; a sensor arranged to detect radiation that is gathered by the miniature objective lens to provide detection signals indicative of the area of the sample.

20 Claims, 6 Drawing Sheets

SYSTEM AND METHOD FOR INSPECTING A SAMPLE USING LANDING LENS

BACKGROUND OF THE INVENTION

FIG. 1 illustrates a prior art metrology or defect review system 10. It includes a rigid structure that carries a sensor (e.g., CCD camera) 12 and a signal collection module such as imaging module 14 (may be optical or charged particle beam optics). The distance between the imaging module 14 and the sample 22 can be 0.1-to few mm or even few cm". this depend the focal length of the objective lens and the distance from the last lens surface and the substrate, and the imaging module 14 usually has a large objective lens that has a radius that exceeds one centimeter and can be large as 20 cm for highly complex lens. Such as objective lens of DUV lens use in semiconductor inspection or metrology equipment.

The rigid structure includes an equipment structure 16 and an equipment frame 20.

Under the imaging module 14, an XYZ stage 26 holds a sample (a substrate such as a wafer or mask) 22. The XYZ stage 26 moves the sample 22 under the imaging module 14. The XYZ stage 26 is supported by interfacing elements 28 positioned between the XYZ stage and a lower surface of the equipment structure 16.

Signal scattered or reflected from the sample 22 are collected by the imaging module sensed by the sensor 12 digitized and processed by a processor (not shown). Further image processing is performed to resolve the feature dimension or the shape a defect on the sample.

For angstrom-level imaging accuracy, mechanical vibrations between the sample 22 and the imaging module 14 is a great obstacle. The mechanical vibrations originate from:
1. Outside the system 10, from the fab (fabrication factory) floor and/or the ambience, by acoustic waves.
2. Internal to the system 10, due to vibratory elements inside the system, such as stepping motors, power supply coolers, air bearing jitter etc.

To reduce the effect of vibration, sophisticated vibration isolation is needed (such as vibration insulators 18 located between the equipment structure 16 and the equipment frame 20, as well as a very rigid structure.

The rigid structure is designed in view of the natural frequency of the mechanical elements. It is desired that the natural frequency exceeds 150 Hz. The higher natural frequency of elements will reduce the undesired shift between the imaging modules and the sample. This means that high stiffness of rigid structure and minimum mass of rigid structure is required. It is quite impractical to achieve higher natural frequency of the rigid structures, due to need to create elements that permit motion, and which use mechanical or air bearings to provide this motion. It is also impractical to resolve angstrom-level elements when the samples are not placed in an extremely quiet and stable condition. This is very difficult because the XYZ stage 26 has to move to new target and settle with zero motion.

There is a growing need to provide a robust evaluation system.

BRIEF SUMMARY OF THE INVENTION

According to various embodiments of the invention there may be provided an evaluation system that may include a miniature module that may include a miniature objective lens and a miniature supporting module; wherein the miniature supporting module is arranged, when placed on a sample, to position the miniature objective lens at working distance from the sample; wherein the miniature objective lens is arranged to gather radiation from an area of the sample when positioned at the working distance from the sample; and a sensor arranged to detect radiation that is gathered by the miniature objective lens to provide detection signals indicative of the area of the sample.

The evaluation system may include a sensor lens positioned between the sensor and the miniature objective lens, wherein sensor lens and the miniature objective lens define a collimated radiation beam zone.

The miniature supporting module is arranged to maintain a spatial relationship between the miniature objective lens and the sample substantially unchanged when the sample is moved in relation to the sensor.

The miniature module may include at least one additional miniature objective lens that is supported by the miniature supporting module.

In various embodiments the working distance may not exceed 1 centimeter, may not exceed 1 millimeter, may not exceed 100 microns, may not exceed 100 nanometers, or may not exceed 10 nanometers.

In some embodiments, the evaluation system wherein a radius of the miniature objective lens may not exceed 1 millimeter; the miniature supporting module may include legs that are arranged to contact the sample, wherein the legs have a micron scale footprint; the miniature module further may include an illumination module; the miniature supporting module may be arranged to support the sensor; and/or the evaluation module may include a stage for mechanically moving the sample in relation to the sensor.

Some embodiments of the invention pertain to a method for inspecting a sample, the method may include positioning a miniature module on the sample; wherein the miniature module may include a miniature objective lens and a miniature supporting module; wherein the miniature supporting module is arranged, when placed on a sample, to position the miniature objective lens at working distance from the sample; wherein the miniature objective lens is arranged to gather radiation from an area of the sample when positioned at the working distance from the sample; illuminating the miniature objective lens with radiation; and detecting, by a sensor, radiation that is gathered by the miniature objective lens to provide detection signals indicative of the area of the sample.

Some embodiments of the invention pertain to an evaluation system that may include a miniature module; a manipulator that is arranged to position the miniature module in a close proximity to a sample; wherein the miniature module may include a miniature objective lens and a miniature supporting module; wherein the miniature supporting module is arranged to be connected to the manipulator so that once positioned in a close proximity to the sample the miniature objective lens is located at working distance from the sample; wherein the miniature objective lens is arranged to gather radiation from an area of the sample when positioned at the working distance from the sample; a sensor arranged to detect radiation that is gathered by the miniature objective lens to provide detection signals indicative of the area of the sample.

Any combinations of any of the components of any of the figures can be provided. Any combination of any of the mentioned above systems can be provided.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

Figure 1:
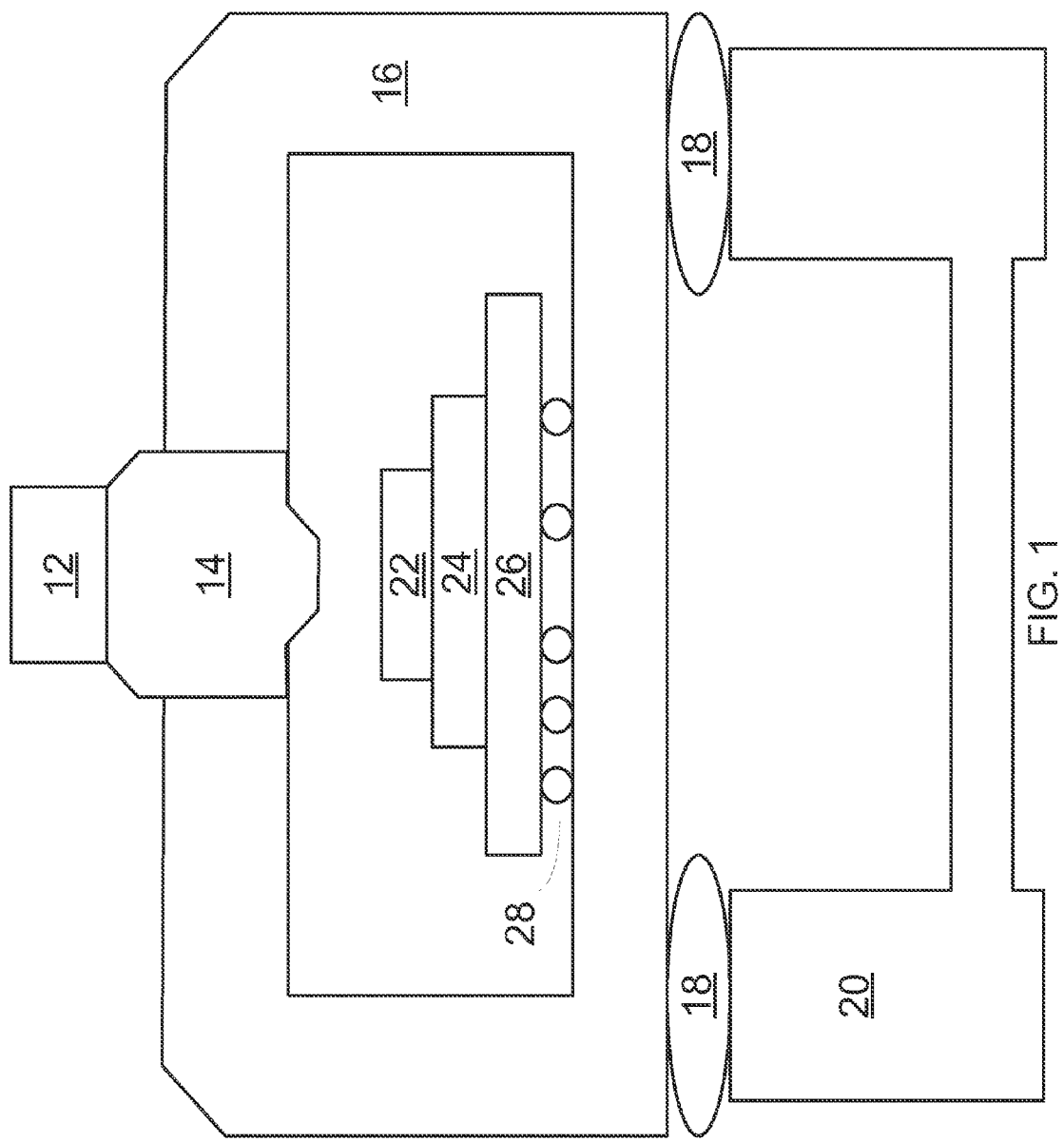
FIG. 1 illustrates a prior art evaluation system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may, for the most part, be implemented using electronic components and modules known to those skilled in the art, details will not be explained in any greater extent than that considered necessary as illustrated above, for the understanding and appreciation of the underlying concepts of the present invention and in order not to obfuscate or distract from the teachings of the present invention.

The assignment of the same reference numbers to various components may indicate that these components are similar to each other.

According to an embodiment there is provided a system in which the large prior art objective lens is replaced by a miniature objective lens that is not mechanically coupled to the rigid structure but is spatially and mechanically separated (decoupled) from the imaging module and the rigid structure, and is either mechanically coupled by a structural element (in a rigid manner) to the sample or is held in proximity to the sample by a manipulator.

The system has the ability to detect an image at noisy condition due to an inherent immunity to vibration obtained by using a miniature objective lens that is mechanically decoupled from the structural of the system, which may be mechanically coupled to the sample and which participates in a formation of a collimated beam zone. Even when the sample vibrates, the image obtained by the miniature objective lens will not move due to the fact that the image is transferred by a collimated beam.

Using a miniature objective lens that is very close to the sample facilitates ultra precise focus which is defined by the working distance between the miniature objective lens and the sample.

The miniature module can be much smaller (for example has a width that is less than 20%, 14%, 10%, 5%, 2% or even less than 1% from the width of the sample) than the sample that is being inspected.

The system provides simple aberration cancelation by having a miniature objective lens and positioning the miniature objective lens very close to the sample—at a very small working distance. This also allows using miniature objective lens with a high numerical aperture.

The working distance may not exceed 1 centimeter, 1 millimeter, 100 microns, 10 microns, 1 microns and may be even smaller than that (10-100 nm for application in which we wish to have the lens very close to the substrate—for example—to enable solid immersion effect or other proximity imaging effects)

The miniature objective lens can be of a hundred-micron scale and belong to a miniature module that can be also very small. The radius of the miniature objective lens can range, for example, between 10 microns and 1 millimeter. (1 mm diameter lens at a distance of few microns from the sample will enable high NA imaging solution)

The miniature objective lens and at least one optical element of the collection optics may form a safe, mechanically decoupled, collimated beam zone in the imaging path—which optically isolates all induced shifts between the imaging module and the miniature objective lens.

This system can enable to integrate high resolution imaging process control module into noisy and/or moving equipment and substrate. For example—an end point image base monitor module can be positioned inside various process chambers.

The miniature objective lens be used in optical or electron optical imaging systems and can be positioned at a very small working distance from the sample—for example about 10-50 microns. The advantage of such short working distances is that the miniature objective lens dimensions are very small, and it is quite easy to eliminate aberrations in such a miniature objective lens. The miniature objective lens, located in some packaging, can be supported by a miniature structural element that is supported by the sample—it is virtually landed on the sample with a positioning accuracy of few microns.

The sample is usually very large in comparison to the miniature objective lens and the various figures may be drawn out of scale. For example, the sample may be a wafer of 200 mm or 300 mm diameter while the miniature objective lens can be less than 1 mm in diameter. The imaging sensor can be as large as needed to enable full signal collection even if the substrate is moving—example: If the landing lens diameter is 1 mm, the collecting lens can be quite big—few centimeters and the sensor also can be few centimeters. Such setup enables collecting signal while the substrate and the landing lens is moving.

The miniature structural element can have a diameter that slightly exceeds 1 mm or below and may have a micron scale footprint.

Figure 2:
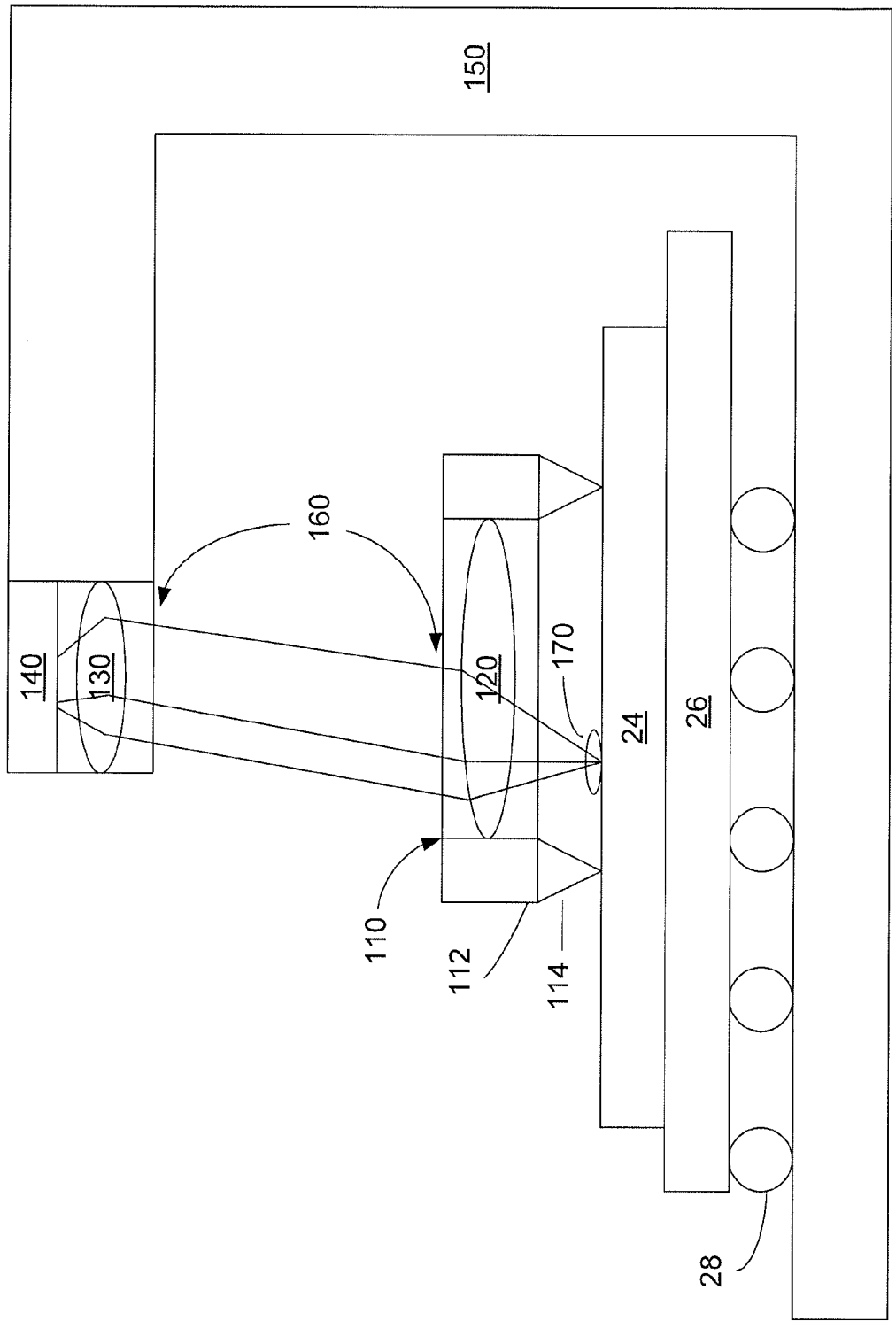
FIG. 2 illustrates an evaluation system according to an embodiment of the invention.

FIG. 2 illustrates an evaluation system 100 according to an embodiment of the invention.

The evaluation system 100 may include:

1. A miniature module 110 that may include one or more miniature objective lenses (such as miniature objective lens 120) and a miniature supporting module 112. The miniature supporting module 112 may be arranged, when placed on a sample 24, to position the miniature objective lens 120 at a working distance from the sample 24. The miniature objective lens 120 may be arranged to gather radiation 170 from an area of the sample 24 when positioned at the working distance from the sample 24.
2. A sensor 140 arranged to detect radiation that is gathered by the miniature objective lens 120 to provide detection signals indicative of the area of the sample 24.
3. A sensor lens 130 positioned between the sensor 140 and the miniature objective lens 120, wherein sensor lens 130 and the miniature objective lens 120 define a collimated radiation beam zone 160 in which a collimated radiation beam propagates.
4. XYZ stage 26.
5. Interfacing elements 28.
6. System structure 150 that may be mechanically coupled to the sensor 140.

The miniature supporting module 112 may be arranged to maintain a fixed spatial relationship between the miniature objective lens 120 and the sample 24 substantially unchanged when the sample 24 is moved in relation to the sensor. The movement may be performed in order to position the miniature module 110 at a desired position in respect to the sensor 140.

The miniature module 110 may include multiple miniature objective lenses—such miniature objective lens 120 and additional miniature objective lens 122 of FIG. 2.

Figure 5:
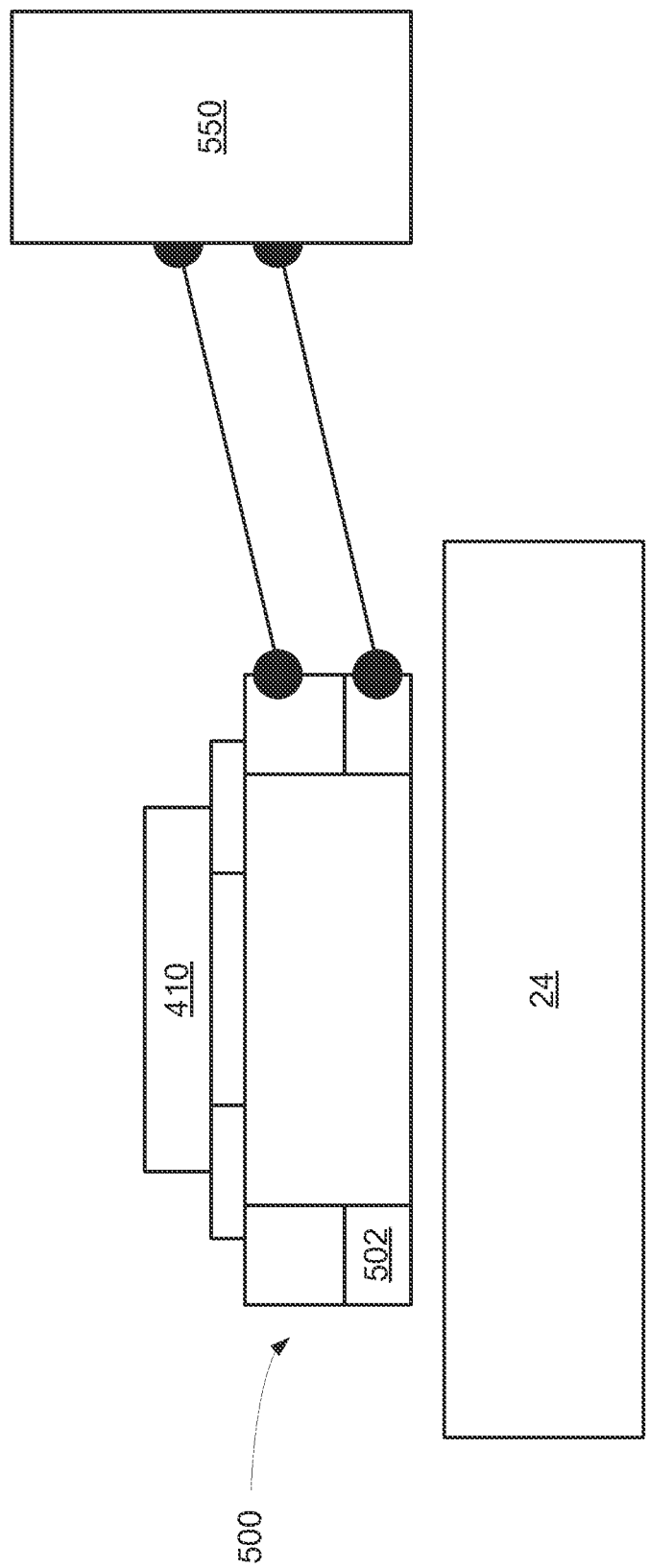
FIG. 5 illustrates a miniature module and a manipulator that holds the miniature module in proximity to a sample, according to an embodiment of the invention.

FIG. 2 illustrates the miniature supporting module 112 as having conical legs 114 that may have a micron scale foot print—they end by micron-scale tips that are positioned on the sample 24. It is noted that the miniature supporting module 112 can also interface with the sample using an air bearing—as illustrated in FIG. 5.

According to another embodiment of the invention the miniature module can include additional optical or sensing components.

The miniature module is expected to remain stationary even when the XYZ stage moves the sample. In order to view different areas of the sample the miniature module can be moved from location to another. The miniature module can be lifted from a current position, positioned above a next position and then lowered to the next position. Additionally or alternatively, multiple miniature lenses can be positioned in proximate to areas of interest and can be removed or moved to other location at an end of an evaluation process or sequence.

Figure 3:
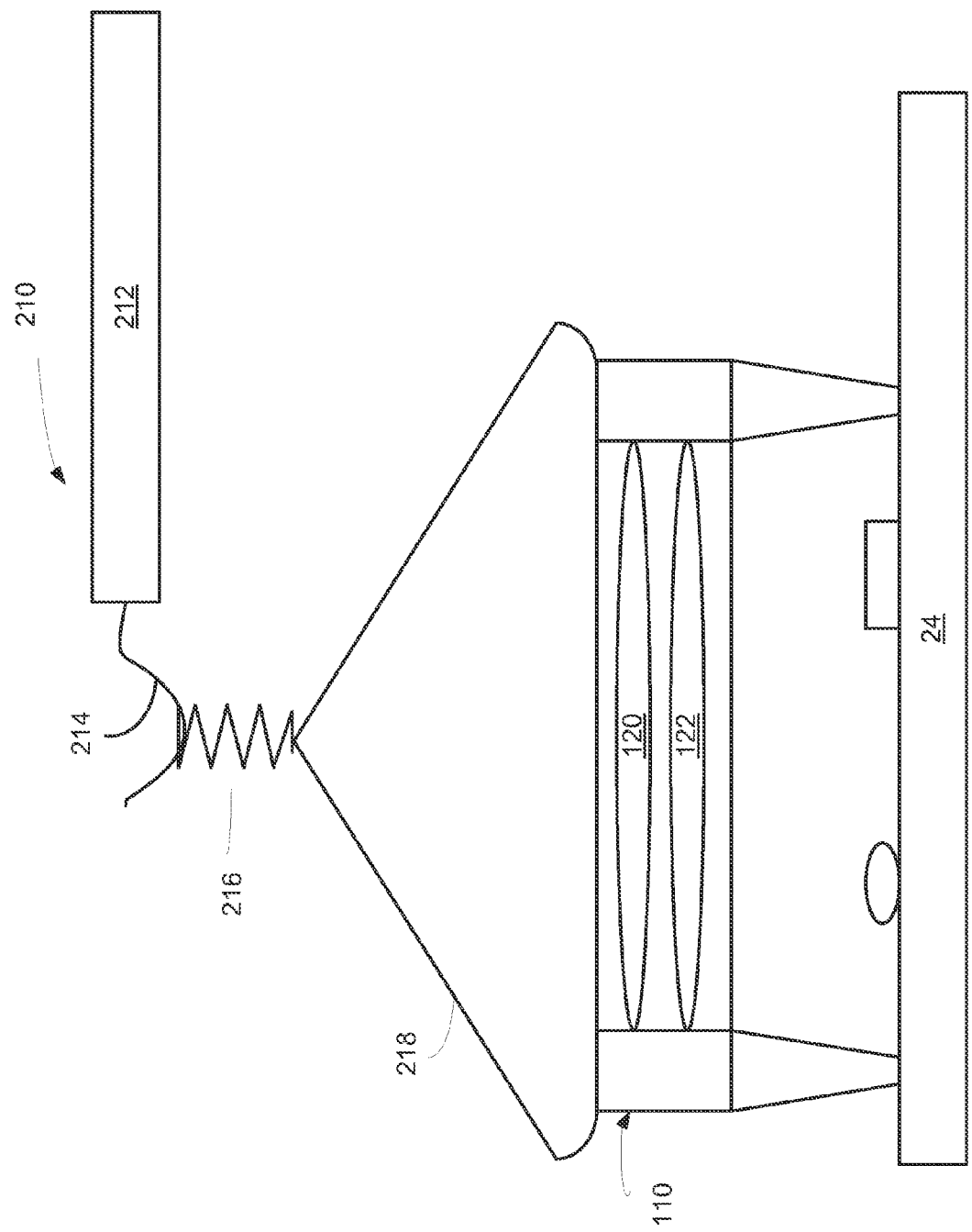
FIG. 3 illustrates a manipulator that positions a miniature module on a sample to be inspected according to an embodiment of the invention.

FIG. 3 illustrates a miniature module 110 and a miniature module positioning module 210 according to an embodiment of the invention. The miniature module positioning module 210 can contact the miniature module 110 and move it from one location to the other. The miniature module positioning module 210 is illustrates as including an arm 212 that can be elevated, lowered and moved within an imaginary XY plane and thereby lift, lower and move the miniature module 110 from one location to the other with minimal contact with the sample 24. The arm 212 has a hook 214 that contacts a spring 216 that in turn is connected to holding arms 218 that may hold the miniature module 110.

The field of view of the miniature objective lens can be large enough (for example- at least few microns wide) to eliminate the need for sub-micron positioning accuracy.

If, for example, the miniature module positioning module 210 positions the miniature module 110 at an accuracy of 5-10 microns, then the field of view of the miniature objective lens can be about 10-50 microns.

Figure 4:
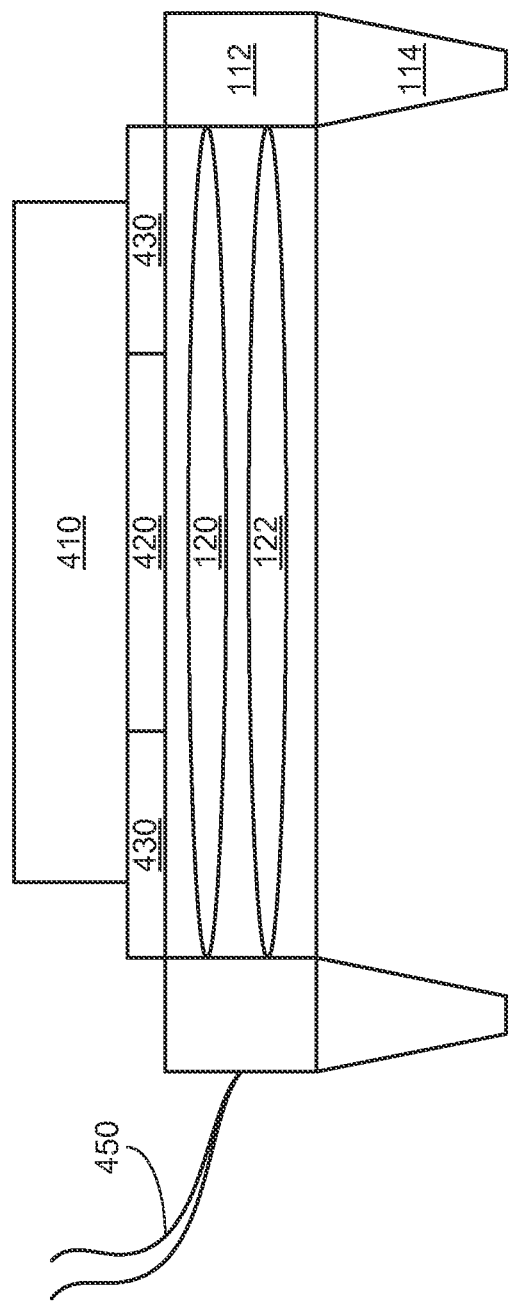
FIG. 4 illustrates an evaluation system according to an embodiment of the invention.

FIG. 4 illustrates a miniature module 400 that includes sensor 410, illumination sources 430 of an illumination module that define an aperture 420 through which radiation from the sample 24 can reach the sensor 410, miniature objective lenses 120 and 122, miniature supporting module 112 that supports the optical components and has legs 114 that may have a micron scale footprint. FIG. 4 also shows flexible wires 450 that can convey power to the miniature module 400, can convey detection signals from sensor 410 and the like. Power can be provided for various reasons such as for driving an electrostatic miniature objective lens, activating the illumination source 430 or sensor 410.

FIG. 5 illustrates a manipulator 550 and a miniature module 500 according to an embodiment of the invention. The miniature module 500 is held in proximity to the sample 24 by a manipulator 550 and interfaces with the sample 24 by air bearing 502. The miniature module 500 can be selected out of any of the miniature modules illustrated in this specification.

Figure 6:
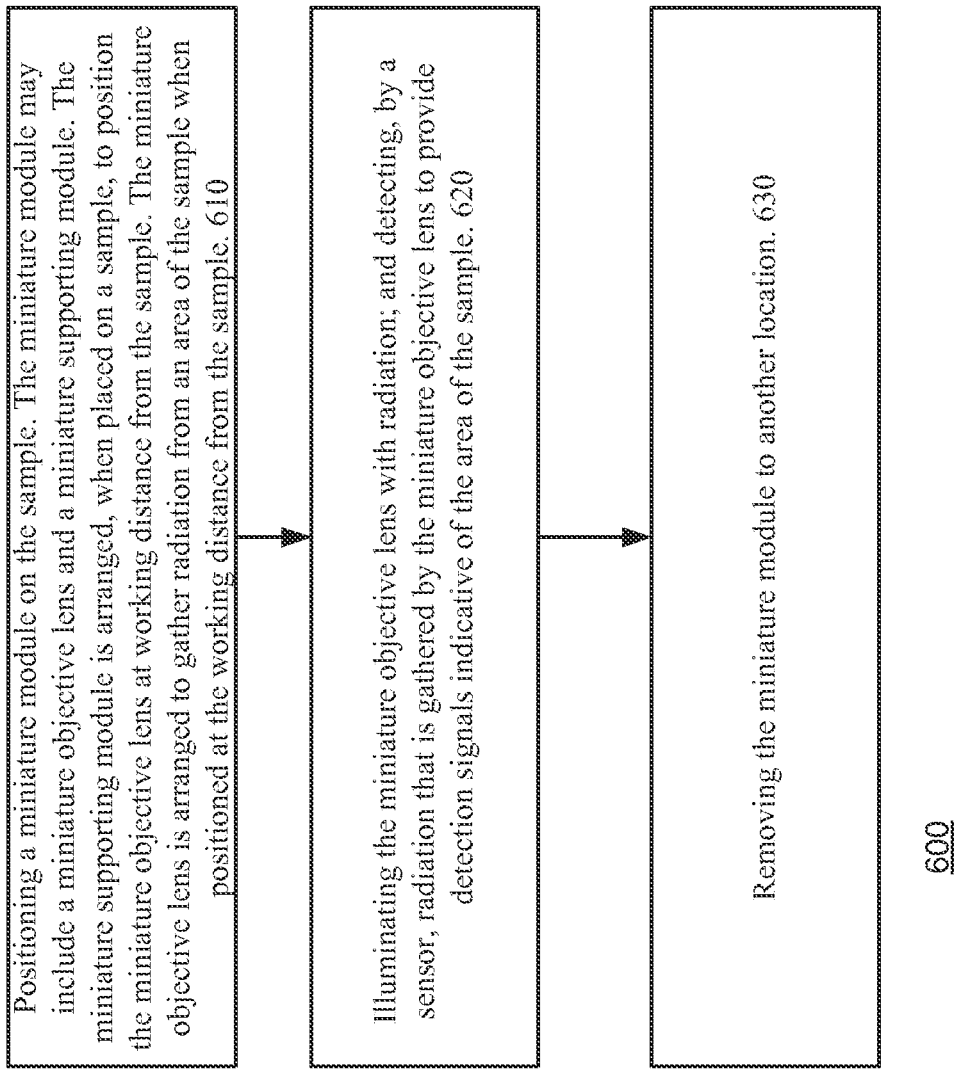
FIG. 6 illustrates a method according to an embodiment of the invention.

FIG. 6 illustrates method 600 for evaluating a sample according to an embodiment of the invention. Method 600 may start by stage 610 of positioning a miniature module on the sample. The miniature module may include a miniature objective lens and a miniature supporting module. The miniature supporting module is arranged, when placed on a sample, to position the miniature objective lens at working distance from the sample. The miniature objective lens is arranged to gather radiation from an area of the sample when positioned at the working distance from the sample.

Stage 610 may be followed by stage 620 of illuminating the miniature objective lens with radiation; and detecting, by a sensor, radiation that is gathered by the miniature objective lens to provide detection signals indicative of the area of the sample.

It is noted that stage 610 may include positioning the miniature module in proximate to the sample by a manipulator without establishing a physical contact between the miniature module and the sample.

Stage 620 may be followed by stage 630 of moving the miniature module to another location (on the sample or not on the sample).

The method may include placing multiple miniature modules on the sample concurrently, moving one or more miniature module from location to the other and the like.

In the foregoing specification, the invention has been described with reference to specific examples of embodiments of the invention. It will, however, be evident that various modifications and changes may be made therein without departing from the broader spirit and scope of the invention as set forth in the appended claims.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or module elements or impose an alternate decomposition of functionality upon various logic blocks or module elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An evaluation system, comprising:
    a support structure;
    a stage coupled to the support structure, the stage configured to support a sample and move the sample in X, Y and Z dimensions;
    an imaging module mechanically coupled to the support structure, the imaging module including a sensor and a sensor lens positioned between the stage and the sensor; and
    a miniature module configured to be placed upon and supported by the sample, the miniature module including a miniature objective lens and a miniature supporting module that positions the miniature objective lens at a working distance from the sample to gather radiation from an area of the sample when the miniature module is placed upon the sample;
    wherein, when the miniature module is placed upon the sample, the miniature objective lens and the sensor lens form a collimated beam zone in an imaging path between the sensor and the sample, the collimated beam zone mechanically separating the imaging module and the miniature objective lens to optically isolate induced shifts between the imaging module and the miniature objective lens, and the sensor detects the radiation gathered by the miniature objective lens to provide detection signals indicative of the area of the sample.

2. The evaluation system according to claim 1, wherein the miniature supporting module is arranged to maintain a spatial relationship between the miniature objective lens and the sample when the sample is moved in relation to the sensor.

3. The evaluation system according to claim 1, wherein the miniature module comprises at least one additional miniature objective lens that is supported by the miniature supporting module.

4. The evaluation system according to claim 1, wherein the working distance does not exceed 1 centimeter.

5. The evaluation system according to claim 1, wherein the working distance does not exceed 1 millimeter.

6. The evaluation system according to claim 1, wherein the working distance does not exceed 100 microns.

7. The evaluation system according to claim 1, wherein the working distance does not exceed 100 nanometers.

8. The evaluation system according to claim 1, wherein the working distance does not exceed 10 nanometers.

9. The evaluation system according to claim 1, wherein a radius of the miniature objective lens does not exceed 1 millimeter.

10. The evaluation system according to claim 1, wherein the miniature supporting module comprises a plurality of legs having micron scale tips that are positioned on the sample when the miniature module is placed upon and supported by the sample.

11. The evaluation system according to claim 1, wherein the miniature module further comprises an illumination module.

12. The evaluation system according to claim 1, wherein the miniature supporting module is further arranged to support the sensor.

13. The evaluation system according to claim 1, wherein the working distance is set to a focal length of the miniature objective lens.

14. The evaluation system according to claim 1, wherein the miniature supporting module comprises an air bearing that interfaces with the sample when the miniature module is placed upon and supported by the sample.

15. The evaluation system according to claim 1, wherein the miniature module has a first width that is less than 20% of a second width of the sample.

16. The evaluation system according to claim 1, further comprising a positioning module configured to elevate the miniature module above the sample, move the miniature module from a first location over the sample to a second location different from the first location, and lower the miniature module onto the sample.

17. The evaluation system according to claim 1, wherein the working distance between the objective lens and the sample when the miniature module is supported by the sample is less than 10 microns.

18. The evaluation system according to claim 1, wherein the sensor lens has a diameter greater than one centimeter.

19. The evaluation system according to claim 1, wherein the miniature objective lens is arranged to collimate the radiation from the area of the sample such that an image formed on the sensor by the miniature objective lens does not move when the sample vibrates.

20. A method for inspecting a sample, comprising:
positioning the sample on a stage, the stage coupled to a support structure and configured to support the sample and move the sample in X, Y and Z dimensions;
positioning a miniature module on the sample; wherein the miniature module comprises a miniature objective lens and a miniature supporting module that positions the miniature objective lens at a working distance from the sample to gather radiation from an area of the sample;
illuminating the miniature objective lens; and
detecting, by an imaging module mechanically coupled to the support structure, the radiation gathered by the miniature objective lens to provide detection signals indicative of the area of the sample, wherein the imaging module includes a sensor and a sensor lens positioned between the sensor and the miniature objective lens, and wherein the miniature objective lens and the sensor lens form a collimated beam zone in an imaging path between the sensor and the sample, the collimated beam zone mechanically separating the imaging module and the miniature objective lens to optically isolate induced shifts between the imaging module and the miniature objective lens.

* * * * *